(12) United States Patent
Falk et al.

(10) Patent No.: US 7,922,488 B2
(45) Date of Patent: *Apr. 12, 2011

(54) METHOD AND APPARATUS FOR ISOLATING A WORK OBJECT

(75) Inventors: Theodore S. Falk, Fresno, CA (US); Thomas E. Bramanti, Fresno, CA (US)

(73) Assignee: Institut Straumann AG, Waldenburg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/401,866

(22) Filed: Mar. 31, 2003

(65) Prior Publication Data

US 2003/0190586 A1    Oct. 9, 2003

Related U.S. Application Data

(63) Continuation of application No. 09/031,440, filed on Feb. 26, 1998, now Pat. No. 6,540,514.

(51) Int. Cl.
*A61C 8/00* (2006.01)
*A61C 9/00* (2006.01)

(52) U.S. Cl. ........................ 433/173; 433/214
(58) Field of Classification Search .......... 433/172–176, 433/214; 206/63.5
See application file for complete search history.

(56) References Cited

U.S. PATENT DOCUMENTS

| | | | |
|---|---|---|---|
| 3,541,689 A | 11/1970 | Snead | |
| 3,827,145 A | 8/1974 | Richards | |
| 4,103,422 A | 8/1978 | Weiss et al. | |
| 4,244,689 A | 1/1981 | Ashman | |
| 4,293,302 A | 10/1981 | Hassler et al. | |
| 4,465,462 A | 8/1984 | Ticknor | |
| 4,522,593 A | 6/1985 | Fischer | |
| 4,531,916 A | 7/1985 | Scantlebury et al. | |
| 4,547,157 A | 10/1985 | Driskell | |

(Continued)

FOREIGN PATENT DOCUMENTS

DE    3110693    9/1982

(Continued)

OTHER PUBLICATIONS

Hess et al., "Esthetic single-tooth replacement with implants: A team approach", Quintessence International, 1998, pp. 77-86, vol. 29, No. 2.

(Continued)

*Primary Examiner* — Cris L Rodriguez
*Assistant Examiner* — Matthew M Nelson
(74) *Attorney, Agent, or Firm* — Brandon N. Sklar, Esq.; Kaye Scholer LLP (57) ABSTRACT

A method for isolating a work object to achieve a predetermined operational objective, the method including the steps of encapsulating at least a portion of the work object in a housing in a work position so as to establish a zone of isolation relative to the portion of the work object; releasibly interconnecting the housing and the portion of the work object so as selectively to maintain said zone of isolation for a period of time sufficient to achieve the predetermined operational objective; and occluding an area proximate to the housing to resist incursion into the area during the period of time. An apparatus for isolating a work object, the apparatus including a housing having an interior dimensioned to permit the housing to be disposed in a work position with the work object received in the interior of the housing; and means for retaining the housing in the work position.

16 Claims, 4 Drawing Sheets

U.S. PATENT DOCUMENTS

| | | | |
|---|---|---|---|
| 4,575,340 | A | 3/1986 | Lustig |
| 4,687,443 | A | 8/1987 | Driskell |
| 4,738,623 | A | 4/1988 | Driskell |
| 4,758,161 | A | 7/1988 | Niznick |
| 4,790,753 | A | 12/1988 | Fradera |
| 4,824,372 | A | 4/1989 | Jorneus et al. |
| 4,838,790 | A | 6/1989 | Koller |
| 4,850,873 | A | 7/1989 | Lazzara et al. |
| 4,854,872 | A | 8/1989 | Detsch |
| 4,906,191 | A | 3/1990 | Soderberg |
| 4,986,753 | A | 1/1991 | Sellers |
| 5,006,069 | A | 4/1991 | Lazzara et al. |
| 5,049,075 | A | 9/1991 | Barrut |
| 5,073,111 | A | 12/1991 | Daftary |
| 5,078,606 | A | 1/1992 | Soderberg |
| 5,104,318 | A | 4/1992 | Piche et al. |
| 5,106,300 | A | 4/1992 | Voitik |
| 5,125,841 | A | 6/1992 | Carlsson et al. |
| 5,135,395 | A | 8/1992 | Marlin |
| 5,154,612 | A | 10/1992 | Carlsson et al. |
| 5,180,303 | A | 1/1993 | Hornburg et al. |
| 5,259,759 | A | 11/1993 | Jorneus et al. |
| 5,286,195 | A | 2/1994 | Clostermann |
| 5,297,963 | A | 3/1994 | Dafatry |
| 5,336,090 | A | 8/1994 | Wilson, Jr. et al. |
| 5,344,457 | A | 9/1994 | Pilliar et al. |
| 5,499,918 | A | 3/1996 | Morgan et al. |
| 5,527,182 | A | 6/1996 | Willoughby |
| 5,540,588 | A | 7/1996 | Earle |
| 5,564,924 | A | 10/1996 | Kwan |
| 5,662,476 | A | 9/1997 | Ingber et al. |
| 5,681,167 | A | 10/1997 | Lazarof |
| 5,725,375 | A | 3/1998 | Rogers |
| 5,749,731 | A | 5/1998 | Morgan et al. |
| 5,762,500 | A | 6/1998 | Lazarof |
| 5,797,741 | A | 8/1998 | Bonpard et al. |
| 5,816,809 | A | 10/1998 | Sapkos |
| 5,829,977 | A * | 11/1998 | Rogers ............................ 433/172 |
| 5,871,358 | A | 2/1999 | Ingber et al. |
| 5,873,722 | A * | 2/1999 | Lazzara et al. ................ 433/173 |
| 5,899,697 | A | 5/1999 | Lazzara et al. |
| 5,904,483 | A * | 5/1999 | Wade ............................ 433/173 |
| 5,906,489 | A | 5/1999 | Khazzam et al. |
| 6,120,293 | A | 9/2000 | Lazzara et al. |
| 6,129,548 | A | 10/2000 | Lazzara et al. |
| 6,135,773 | A | 10/2000 | Lazzara |
| 6,142,782 | A | 11/2000 | Lazarof |
| 6,217,331 | B1 | 4/2001 | Rogers et al. |
| 6,227,856 | B1 | 5/2001 | Beaty et al. |
| 6,325,628 | B1 | 12/2001 | Morgan |
| 6,394,809 | B2 | 5/2002 | Rogers et al. |
| 6,540,514 | B1 | 4/2003 | Falk et al. |
| 6,565,357 | B1 | 5/2003 | Lazzara et al. |

FOREIGN PATENT DOCUMENTS

| | | |
|---|---|---|
| EP | 0 139 052 A1 | 5/1985 |
| EP | 0 190 670 A2 | 8/1986 |
| EP | 0 313 222 A2 | 4/1989 |
| EP | 0 423 798 A1 | 4/1991 |
| EP | 0 473 262 A1 | 3/1992 |
| ES | 2051239 | 6/1994 |
| FR | 81 17607 | 12/1982 |
| WO | WO-82/03762 | 11/1982 |
| WO | WO-88/03391 | 5/1988 |

OTHER PUBLICATIONS

Higginbottom, Frank, "Transfer System for Cement-Retained Restorations on Nonsubmerged Dental Implants", QDT, 1997, pp. 55-61.

Belser et al., "Implant-Supported Restorations In The Anterior Region: Prosthetic Considerations", Practical Periodontics and Aesthetic Dentistry, Nov./Dec. 1996, pp. 875-882, vol. 8, No. 9.

Hess et al., "Asthetischer Einxelzahnersatz mit Implanten-ein Team Approach", Implantologie, 1996, 3, pp. 245-256.

Saunders et al., "Protective Cover Cap for Implant Attachment", The Journal of Prosthetic Dentistry, Dec. 1993, pp. 548-549, vol. 70 No. 6.

Sutter et al., "The New Restorative Concept of the ITI Dental Implant System: Design and Engineering", The International Journal of Periodontics & Restorative Dentistry, Oct. 1993, pp. 409-431, vol. 13 No. 5.

Nobelpharma, "Temporary Components", Brochure, 1992, total 4 pages, Nobelpharma, Goteborg, Sweden.

Jennings, Kevin, "ITI Hollow-Cylinder and Hollow-Screw Implants: Prosthodontic Management of Edentulous Patients Using Overdentures", The International Journal of Oral & Maxillofacial Implants, 1991, pp. 202-206, vol. 6 No. 2.

Babbush, C.A., "Titanium Plasma Spray Screw Implant System for Reconstruction of the Edentulous Mandible", Dental Clinics of North America, Jan. 1986, pp. 117-131, vol. 30 No. 1.

Babbush et al., "A Solution For The Problematic Atrophic Mandible: The Titanium Plasma Spray (TPS) Screw Implant System", Gerodontics, 1986, pp. 16-23, vol. 2.

Yalisove, Irving, "Crown and Sleeve-Coping Retainers For Removable Partial Prostheses", Journal of Prosthetic Dentistry, Nov.-Dec. 1966, pp. 1069-1085, vol. 16 No. 6.

Maynard et al; "Physiologic Dimensions of the Periodontium Significant to Restorative Dentist", Journal of Periodontology, Published by the American Academy of Periodontology, pp. 170-174, vol. 50, No. 4, Apr. 1979.

Spiekermann et al; "Implantology", Color Atlas of Dental Medicine, New York, 1995.

Lang et al; "The Relationship Between the Width of Keratinized Gingiva and Gingival Health", Journal of Periodontology, Published by the American Academy of Periodontology, pp. 623-627, vol. 43, No. 10, Oct. 1972.

\* cited by examiner

FIG. 11

METHOD AND APPARATUS FOR ISOLATING A WORK OBJECT

This is a Continuation of application Ser. No. 09/031,440 filed Feb. 26, 1998 now U.S. Pat. No. 6,540,514 which claims priority to Disclosure document No. 413,619 filed Jul. 15, 1997.

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to a method and apparatus for isolating a work object and, more particularly, to such a method and apparatus which are operable with particular utility in surgical and other medical techniques and particularly those involving osseointegration.

2. Description of the Prior Art

A variety of surgical procedures have long been employed to restore, or reinforce, the physiological integrity of living creatures, and particularly of human beings. While the earliest such surgical techniques focused on the restoration of, for example, the human skeletal structure, the same basic techniques have application to a wide variety of surgical and other medical applications with significant beneficial effect.

It is known, for example, to use the technique of osseointegration to unite bone fragments for the purpose of restoring an arm, leg or other skeletal structure. This technique has been employed with beneficial effect in a wide variety of applications including, more recently, in the establishment of dental implants. For example, the Lazzara, et al. U.S. Pat. Nos. 4,846,683 and 4,850,870 disclose, respectively, prosthodontic restoration techniques which employ osseointegration to achieve attachment of the individual dental implants. These patents are merely representative of a wide variety of techniques, both patented and otherwise in usage, which permit the implacement of dental appliances at locations and with a permanency not heretofore achieved using prior art surgical techniques.

It is apparent, however, that the use of such surgical techniques, whether for dental surgery or other surgical or medical purposes, presents difficulties which may not only interfere with the long term success of the technique, but may also cause unwarranted pain and other discomfort for the patient during the recovery period. More specifically, in the case of dental implant surgery, a condition develops because of the passage of time required for the osseointegration to be achieved. It is inherent in this surgical technique that a period of several months is required for the implant to join with the bone structure by the very process of osseointegration. It is also necessary to provide sufficient time for the dental restoration to be prepared by a dental laboratory. During this period of time, other physiological development occurs which may interfere, or complicate, the subsequent surgical procedures. The discomfort and pain of the patient experienced during these surgical procedures is well known and the long term success of the surgical procedure may be compromised. More specifically, the gum tissue proximate to the location in which the dental implant is undergoing osseointegration, and thereafter before the permanent dental appliance is installed, continues to grow and occludes the site of the implant. The natural tendency is for such gum tissues invade and to overlay the site of the implant during this period of time. After osseointegration has taken place, a solid abutment is attached to the implant. The dental appliance is subsequently attached to the abutment. It is required that the incursion of gum tissue be displaced from the location of the implant to permit the solid abutment and subsequently the dental appliance to be permanently affixed to the location. Typically, the removal of such gum tissue requires that the gum tissue be incised and extracted from the site to expose the implant and the area required for the abutment and dental appliance to be installed. This surgical procedure, of course, causes discomfort and pain to the patient as well as presenting the opportunity for infection and other medical complications which may significantly interfere with the overall success of the surgical procedure.

Therefore, it has long been known that it would be desirable to have a method and apparatus for isolating a work object which have particular utility in the practice of surgical and other medical procedures employing the technique of osseointegration; which operate to ensure that the negative consequences experienced with the use of such surgical techniques are minimized; which have particular utility in the surgical techniques employed in the use of osseointegration in the establishment of dental implants; which operate to secure the surgical area over the lengthy period required for osseointegration to take place and subsequent surgical procedures to be performed; which are fully compatible with surgical techniques presently employed in osseointegration, whether dental or for other specific purposes; and which are otherwise fully capable of achieving their respective operational objectives.

BRIEF SUMMARY OF THE INVENTION

Therefore, it is an object of the present invention to provide an improved method and apparatus for isolating a work object.

Another object is to provide such a method and apparatus which are adapted to usage in surgical and other medical techniques wherein the surgical area must conventionally be restored to a predefined condition in order for subsequent surgical, or other medical procedures, to be preformed.

Another object is to provide such a method and apparatus which are particularly well suited to usage in all surgical techniques in which osseointegration is employed thereby requiring the passage of time to achieve integration between the medical appliance and the bone structure.

Another object is to provide such a method and apparatus which are uniquely well suited to usage in such surgical techniques where the passage of time results in the incursion of tissue into the surgical area conventionally requiring removal, or displacement, in order to permit subsequent surgical procedures to be performed.

Another object is to provide such a method and apparatus which possess the ability to preserve a surgical area over a lengthy period of time for the subsequent performance of restorative techniques, surgical techniques, or other medical procedures, in the surgical area while reducing to an absolute minimum the susceptibility of the surgical area to infection, or other medical incapacity.

Another object is to provide such a method and apparatus which significantly enhance both the comfort of the patient and the likelihood of complete success in the performance of surgical producers.

Another object is to provide such a method and apparatus which are fully compatible with conventional surgical and medical procedures and devices.

Another object is to provide such a method and apparatus which require little specialized training so as to permit their adoption expeditiously and at minimal cost.

Further objects and advantages are to provide improved elements and arrangements thereof in an apparatus for the purpose described which is dependable, economical, durable and fully effective in accomplishing its intended purposes.

These and other objects and advantages are achieved, in the preferred embodiment of the present invention, in a method for isolating a work object to achieve a predetermined operational objective, the method including the steps of: encapsulating at least a portion of the work object in a housing in a work position so as to establish a zone of isolation relative to the portion of the work object; and occluding an area proximate to the housing to resist incursion into the area during a predetermined period of time.

DETAILED DESCRIPTION OF THE INVENTION

Figure 2:
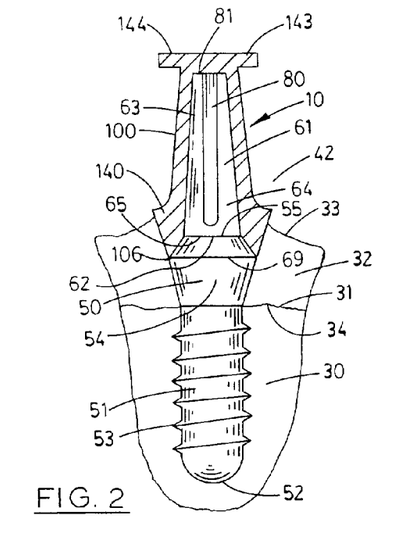
FIG. 2 is a somewhat enlarged fragmentary vertical section of a work position depicted in FIG. 1 with the apparatus of the present invention installed in accordance with the method of the present invention and shown in larger than actual size.

Referring more particularly to the drawings, the apparatus of the present invention is generally indicated by the numeral 10 in FIG. 2.

The method and apparatus of the present invention are adapted for usage in a wide variety of environments and are particularly well suited to usage in surgical and other medical procedures such as where osseointegration is employed to reconstruct bone structure, tissue and the like in living organisms and, most particularly, human beings. In such surgical environments of usage, typically the restoration is accomplished through the use of pins, screws or other fastening devices which are implanted in predetermined locations and allowed to knit in those positions by the integration of the living bone matter and tissue with the implant. Such osseointegration requires typically several months to be achieved and must be accomplished for any subsequent surgical procedures can be performed.

In the illustrative environment hereof the method and apparatus of the present invention are employed with dental implant procedures such as, for example, of the type developed by Institut Straumann A.G. of Switzerland, Implant Innovations, Inc. and of other types such as shown and described in the prior art patents made of record in this case.

Figure 1:
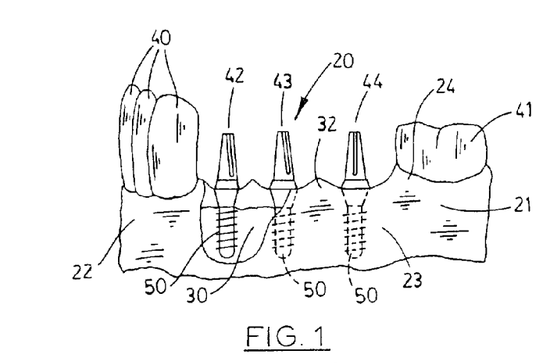
FIG. 1 is a fragmentary side elevation of the lower jaw, or mandible, of a patient representing a typical operative environment within which the method and apparatus of the present invention can be employed.

In the illustrative environment shown herein, the mouth of a patient is shown fragmentarily in FIG. 1 and generally indicated by the numeral 20 therein. As shown therein, the lower jaw of the mouth of the patient is generally indicated by the numeral 21 and may be viewed as having a proximal portion 22 and lateral extremities 23. The lower jaw has an upper portion 24.

More specifically, the lower jaw 21 has a lower jawbone, or mandible, 30, with an upper surface 31, as shown in FIG. 2. The lower jawbone is encased in gum tissue 32 which, for purposes of describing the method and apparatus of the present invention may be viewed as having an exterior surface 33 and an interior surface 34 contiguous with the lower jawbone.

For purposes of illustrative convenience, as shown in FIG. 1, lower front teeth, or incisors, are generally indicated by the numeral 40 and a lower back tooth, or molar, by the numeral 41. Between the lower front teeth and the lower back tooth, a first work position, second work position and third work position are generally indicated by the numerals 42, 43 and 44, respectively.

A work object or dental implant is generally indicated by the numeral 50 in the several views. For purposes of illustrative convenience, it will be understood that the dental implant 50 shown in FIGS. 2, 3, 4 and 7 is the dental implant shown in the first work position 42 in FIG. 1. The dental implant 50 has a lower or base portion 51 which, in accordance with prevailing surgical procedures, has been screw-threadably inserted in the lower jawbone 30 in the first work position 42. The base portion has a distal end portion 52 and an externally screw threaded portion 53. The base portion has a proximal end portion 54 having a flat upper surface 55 which, at the time of the surgical implanting procedure, is disposed in coplanar relation to the upper surface 31 of the lower jawbone 30. It will be understood that an externally screw threaded bore extends into the flat upper surface 55 of the base portion and extends axially of the base portion a predetermined distance.

The dental implant 50 has an upper, or abutment portion, generally indicated by the numeral 61 and having a distal end portion 62. The abutment portion has a tapered upper portion 63 having a substantially conical outer surface 64. The abutment portion has a flat lower surface 65. As can be visualized in FIG. 2, the abutment portion 61 and base portion 51 can be separated from each other, as will hereinafter be described, along a plane defined by the upper surface 55 of the base portion and lower surface 65 of the abutment portion.

Returning again to the structure of the base portion 51 of the dental implant 50, the proximal end portion 54 has an annular collar or shoulder 66 extending thereabout. The annular shoulder may be viewed as having a lower divergent surface 67 and an upper convergent surface 68. The lower divergent surface and upper convergent surface are separated by an annulus or annular ridge 69 which extends about the annular shoulder defining a plane right-annularly related to the longitudinal axis of the dental implant and concentric thereto.

A groove 80 is formed in the outer surface 64 of the tapered upper portion 63 of the abutment portion 61 extending therealong to a terminal surface 81 defining a plane right-angularly related to the longitudinal axis of the dental implant 50.

Figure 8:
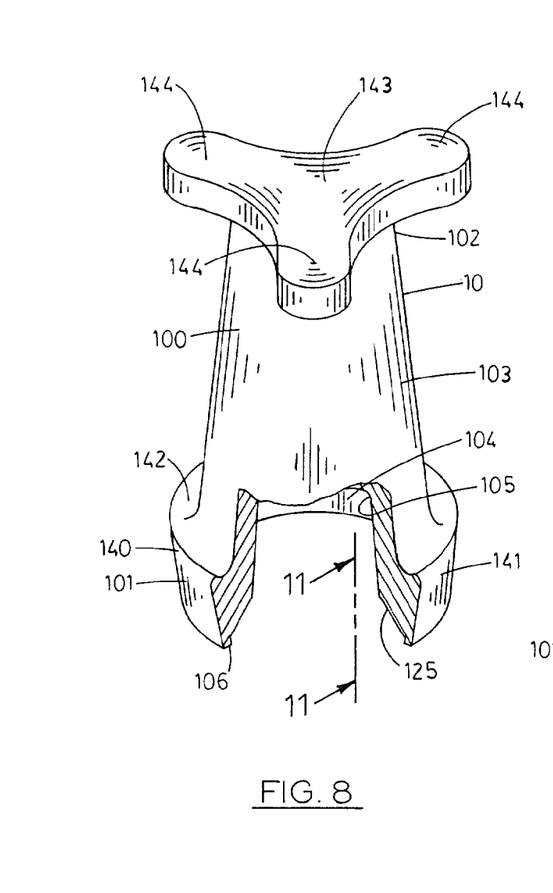
FIG. 8 is a somewhat enlarged, fragmentary perspective view of the embodiment of the apparatus of the present invention depicted in FIGS. 2 and 3.
Figure 9:
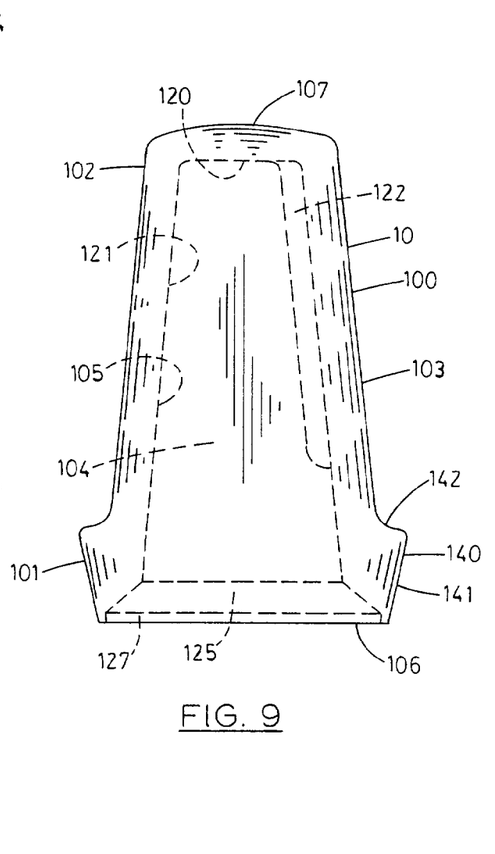
FIG. 9 is a side elevation of a second embodiment of the apparatus of the present invention depicted in FIG. 4.

The apparatus 10 employed in the practice of the method of the present invention is shown herein in two embodiments shown respectively in FIGS. 8 and 9. For illustrative convenience, the two embodiments of the invention are described herein together.

The apparatus 10 of the two embodiments has a body portion or housing 100 which can be fabricated of any suitable material. In the preferred embodiment, the housing is constructed of a thermal injected plastic material such as Bayer 348ABS medical grade plastic which is molded in the configuration hereinafter described. In this regard it will be understood that the housing, as shown in the drawings hereof, is larger than actual size for purposes of more clearly disclosing the structure thereof.

Figure 4:
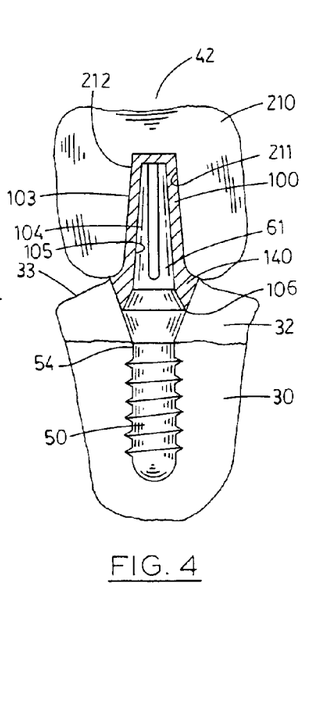
FIG. 4 is a fragmentary vertical section of the work position shown in FIGS. 2 and 3 and showing the apparatus of the present invention and a temporary dental appliance employed in accordance with a subsequent step in the practice of the method of the present invention.

The housing 100 may be viewed as having a distal portion 101 and an opposite proximal portion 102. The housing has an outer surface 103 and encloses an interior chamber 104 defined by an interior surface 105. As best shown in FIG. 4, the interior surface 105 is configured so as preferably to conform to the outer surface 64 of the abutment portion 61 of the dental implant 50 in fitted relation. The housing has a lower annulus 106 and an upper end wall 107.

The interior surface 105 of the housing 100 has a terminal surface 120. A convergent surface 121 extends upwardly to communicate with the terminal surface 120. As shown in FIG. 9, a ridge portion 122 is formed in the convergent surface 121 and dimensioned and so configured as to mate with the groove 80 of the abutment portion 61 of the dental implant 50. The interior surface 105 has an interior annulus 123 at the lower end of the convergent surface 121 and outwardly from which is extended in interior shoulder surface 124. A sloped interior annular surface 125 extends downwardly and outwardly therefrom to an interior annulus 126. The interior annulus 126 has an interior annular surface 127 shown best in FIG. 11. The interior annular surface is sloped in downwardly converging relation so as to permit the lower annulus 106 to be snap fitted on the annular ridge 69 of the annular shoulder 66 of the base portion 51 of the dental implant 50.

The housing 100 has an annular shoulder 140 which is of thickened proportions so as to occupy a predetermined amount of space, as can best be visualized in FIGS. 8 and 9. The annular shoulder has a sloped annular surface 141 and a beveled upper surface 142. As can be visualized in FIGS. 2, 3 and 4, the configuration and dimensions of the annular shoulder 140 are, in the preferred embodiments, such as to occupy sufficient space to prevent the gum tissue 32 from incursion into the area bounding the annular shoulder 66 of the base portion 51 of the dental implant 50, as will hereinafter be described in greater detail. A wide variety of other embodiments can be employed in the method and apparatus of the present invention.

As previously noted, two embodiments of the apparatus 10 of the present invention are depicted in the drawings, those being in FIGS. 8 and 9. In the embodiment shown in FIG. 8, the housing 100 has a grasping portion 143 mounted on and integral with the upper end wall 107 of the housing 100. The grasping portion has multiple prongs 144, in this example three prongs, extending outwardly from the longitudinal axis of the housing 100, as best shown in FIG. 8.

Figure 5:
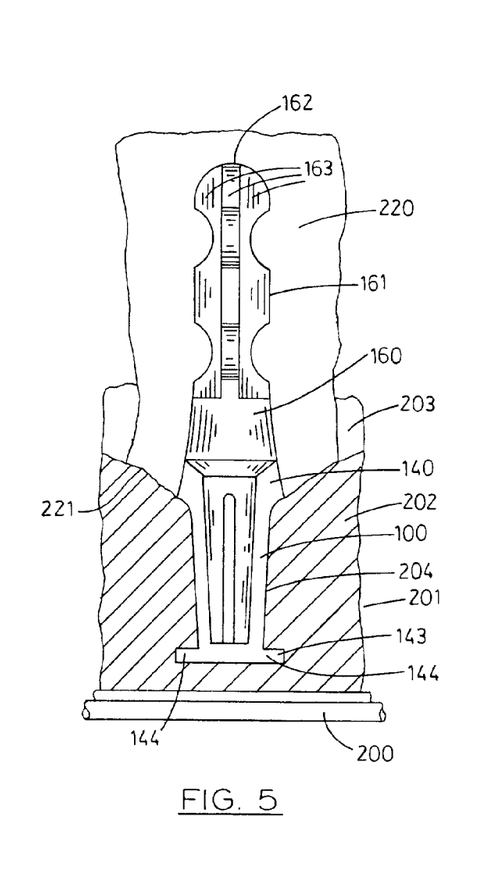
FIG. 5 is a somewhat enlarged fragmentary vertical section of the impression tray shown in FIG. 3 and employed in a subsequent step in the practice of the method of the present invention employing, additionally, an implant analog.
Figure 6:
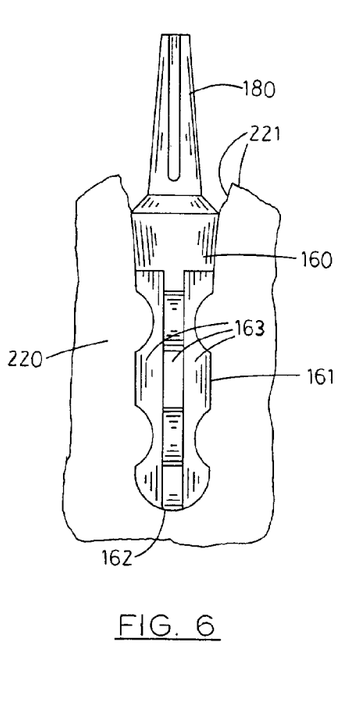
FIG. 6 is a fragmentary vertical section of the implant analog depicted in FIG. 5 and employed in an inverted attitude for purposes of the practice of a subsequent step in the method of the present invention.
Figure 10:
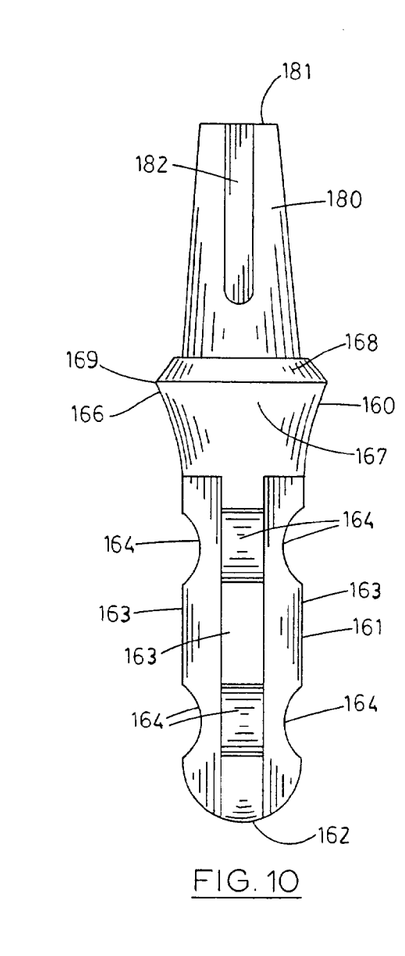
FIG. 10 is a somewhat enlarged side elevation of the implant analog depicted in FIGS. 5 and 6.

The method of the present invention employs an implant analog generally indicated by the numeral 160 in FIGS. 5, 6 and 10. The implant analog has a base portion 161 extending to a distal end portion 162 and having four rib portions 163 disposed at 90 degrees relative to each other. Each of the rib portions has a pair of arcuate recesses 164. An annular collar or shoulder 166 extends upwardly from the rib portions 163 and includes a lower divergent surface 167 and an upper convergent surface 168 separated from each other by an annulus or ridge 169. It will be seen that the annular shoulder 166 is so dimensioned and configured as to be identical to the annular shoulder 66 of the dental implant 50.

The implant analog 160 has an abutment portion 180 extending to a terminal surface 181 and having a groove 182 so configured and dimensioned as to conform to the ridge portion 122 of the convergent surface 121 of the interior surface 105 of the apparatus 10 and thus to the groove 80 of the dental implant 50.

For illustrative convenience in describing the method of the present invention and the use of the apparatus 10 hereof, reference is had in several of the views of the drawings to other elements to illustrate the environment of usage of the method and apparatus of the present invention. Thus, in FIG. 3 an impression tray 200 is fragmentarily shown therein defining an interior 201 containing mold material 202. The outer surface of the mold material or, in other words, the impression made thereby is indicated at 203 and, if desired, an adhesive layer coating the apparatus 10 of the present invention can be employed which is generally indicated by the numeral 204.

Referring more particularly to FIG. 4, a temporary dental appliance or crown is generally indicated by the numeral 210 into which a passage or interior 211 extends dimensioned to fit the outer surface 103 of the housing 100 of the apparatus 10. As shown in FIG. 4, an adhesive layer is generally indicated by the numeral 212.

Referring more particularly to FIG. 5, dental stone is generally indicated by the numeral 220. The surface of the dental stone providing the impression model is indicated by numeral 221.

Figure 7:
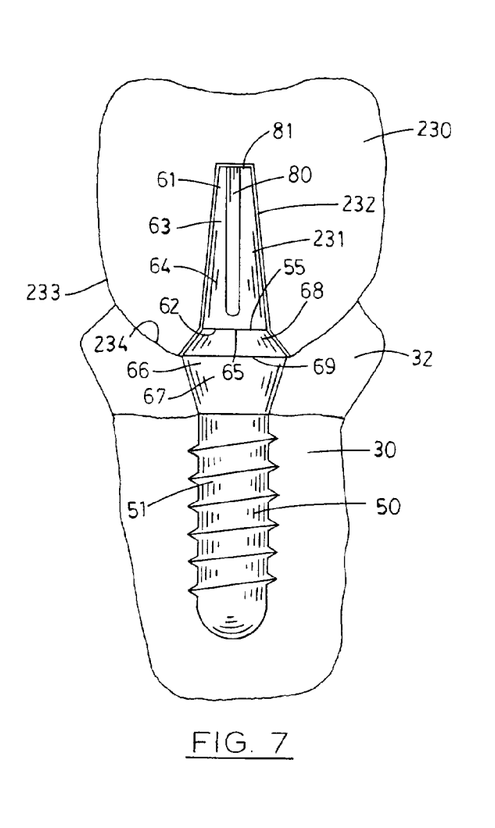
FIG. 7 is a somewhat enlarged fragmentary vertical section of the work position depicted in FIGS. 2, 3 and 4 showing a permanent crown mounted on the dental implant in accordance with a subsequent step in the practice of the method of the present invention.

Referring then finally to FIG. 7, a permanent dental appliance or crown is generally indicated by the numeral 230. A passage or interior 231 extends into the permanent crown and is dimensioned to conform to the outer surface 64 of the abutment portion 61 of the dental implant 50. An adhesive layer 232 attaches the permanent crown on the outer surface 64. As shown therein, the outer surface of the permanent crown is indicated by the numeral 233. The surface of the gum tissue 32 about the permanent crown is indicated by the numeral 234.

Operation

The operation of the described embodiments of the subject invention and the method hereof are believed to be clearly apparent and are briefly described hereinafter.

In the method of the present invention, one or more dental implants 50 are installed in the upper and/or lower jawbone of the patient using otherwise conventional surgical or medical techniques. For illustrative convenience, and as previously described, the dental implant 50 occupying first work position 42, as shown in FIG. 1, will be assumed to be the site described. It will be understood, however, that the method of the present invention can be employed on one or more other work positions by varying the procedures accordingly.

Again, using conventional surgical procedures, the dental implant 50 occupying the first work position 42 is permitted to osseointegrate with the lower jawbone 30 for a period of several months. When this condition has been achieved, the dental implant is ready to receive occlusal load and be restored by conventional dental means. The cover screw, not shown, which covers the entrance into the dental implant 50 is removed and the internal aspect is irrigated with an antimicrobial solution. The soft gum tissues and their integrity and position in relation to the collar of the dental implant are evaluated along with the interocclusal space between the dental implant or collar or shoulder and the opposing dentition.

An appropriate height for the abutment portion 61 of the dental implant 50 is selected such as, for example, 4.0 millimeters, 5.5 millimeters, or 7.0 millimeters. The selected abutment portion is inserted into the internal aspect of the dental implant base portion 51 and screwed in a clockwise direction into place using an appropriate carrier device, not shown. The abutment portion 61 is tightened to 35 Ncm of pressure using a torque wrench moved in a clockwise direction. The abutment portion 61 and the annular collar or shoulder 66 of the base portion 51 are then isolated and dried.

Figure 11:
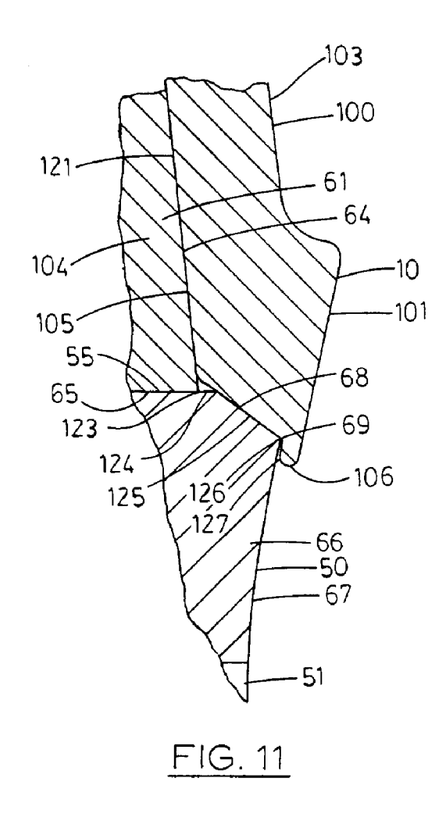
FIG. 11 is a somewhat further enlarged fragmentary vertical section taken from a position indicated by line 11-11 in FIG. 8.

The apparatus 10 of the present invention is then positioned in covering relation to the abutment portion 61 and pressed downwardly until the lower annulus 106 snaps into place in fitted engagement with the annular ridge 69 of the annular collar 66 of the base portion 51, as shown in FIGS. 2 and 11.

Subsequently, the apparatus 10 is coated with a suitable adhesive and is roughened on the surface thereof to produce undercuts and grooves permitting retention in dental impression material. The prongs 144 also operate to retain the apparatus 10 in the dental impression material. Either or both of the undercuts and grooves on the one hand and/or the prongs on the other can be employed for this purpose.

Figure 3:
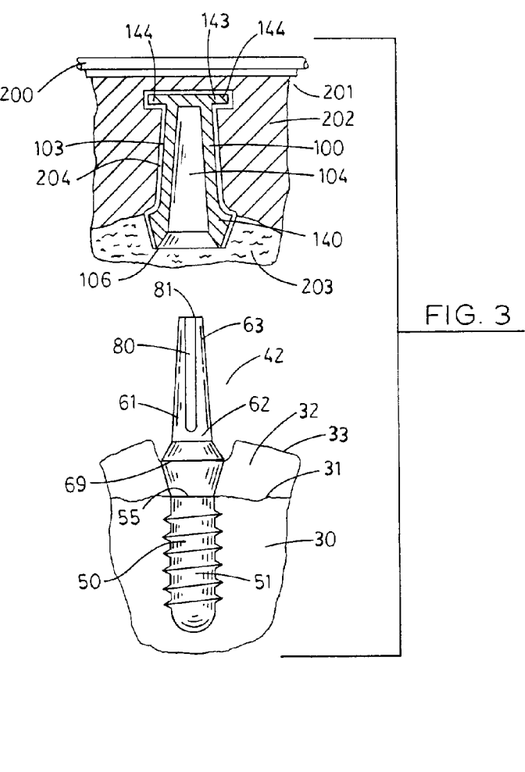
FIG. 3 is a somewhat reduced fragmentary vertical section showing the work position of FIG. 2 and depicting a subsequent step in the practice of the method of the present invention, producing a dental impression using an impression tray.

Referring to FIG. 3, the impression tray 200 containing dental impression material 202 in the interior 201 thereof is positioned in the patient's mouth 20 to make a mold of the apparatus 10, the adjacent teeth, the adjacent soft tissues and the opposing dentition. After an appropriate period of setting and hardening time, the impression tray is removed from the patient's mouth containing a mold of the teeth and removing the apparatus 10 from the dental implant 50 as shown in FIG. 3.

Referring next to FIG. 4, a second apparatus 10 preferably of the form shown in FIG. 9, is trimmed to match the height of the abutment portion 61 and is snap fitted into the position shown in FIG. 4 again engaging the annular ridge 69 of the base portion 51. The second apparatus 10 is used as a base for construction of the dental temporary restoration lined with dental acrylic and/or a temporary cement material. The temporary dental appliance or crown 210 is then mounted on the second apparatus 10, as shown in FIG. 4. It will be seen that the annular shoulder 140 of the apparatus 10 operates to occlude the area bounding the annular shoulder 66 of base portion 51 so as to prevent the gum tissue 32 from growing into or otherwise occupying the area.

In the meantime, the impression mold 203 is sent to a dental laboratory for fabrication of the dental restoration which will be mounted on the dental implant 50. During this procedure, the implant analog 160 is inserted into the interior chamber 104 of the housing 100 of the apparatus 10, as shown in FIG. 5. Sufficient pressure is exerted to cause the implant analog to snap into place with the lower annulus 106 of the housing 100 snapping over the annular ridge 169 of the annular shoulder 166 of the implant analog 160.

Then, using conventional laboratory techniques, dental laboratory gypsum stone is mixed and poured into the impression 203 to reproduce a mold of the patient's mouth and implant suprastructure. After a period of setting time, the dental stone hardens and the impression tray is separated therefrom retaining the apparatus 10 of the present invention in the mold material 202 and leaving the implant analog 160 in the resulting dental stone 220, as best shown in FIG. 6.

At this time, a third apparatus 10 of the present invention is trimmed to match the height of the implant analog in the dental stone 220 and inserted onto the abutment portion 180 of the implant analog until it snaps into place as previously described. This third apparatus 10 of the present invention is used as a waxing base for the construction of the dental restoration. Wax is applied directly onto the third apparatus 10 and carved to simulate the final tooth morphology, sprued, invested in dental burn-out investment and cast with metal alloys using the wax burn-out casting technique. The final restoration is polished, coated with porcelain or other suitable material and prepared for final installation in the patient's mouth.

The resulting permanent crown 230, as described in the illustrative example shown in FIG. 7, is ready for installation. The second apparatus 10 and temporary crown 210 are removed from the dental implant 50 from the position shown in FIG. 4. The area is irrigated with an antimicrobial solution. The soft tissues and their integrity and position in relation to the collar of the implant are also evaluated. The final restoration is seated on the abutment portion 61 of the dental implant 50 and the interproximal contact areas and occlusal contacts are adjusted to the desired fit. The adjusted permanent crown 230 is removed, the dental implant 50 is isolated and dried. The permanent crown 230 is filled with dental cement and then seated directly on the abutment portion 61 of the dental implant 50. The cement is permitted to set for several minutes, excess cement is removed from the annular shoulder 66 of the base portion 51 and the area is irrigated once again with antimicrobial solution. Subsequently a dental radiograph is taken to confirm seating of the restoration and removal of the excess cement.

Therefore, the method and apparatus for isolating a work object of the present invention having particular utility in the practice of surgical procedures employing the technique of osseointegration; operate to ensure that the negative consequences experienced with the use of such surgical techniques are minimized; have particular utility in the surgical techniques employed in the use of osseointegration in the establishment of dental implants; operate to secure the surgical area over the lengthy period required for osseointegration to take place; are fully capable with surgical techniques presently employed in osseointegration in all surgical procedures, whether dental or for other specific purposes; and are otherwise fully capable of achieving their operational objectives.

Although the invention has been herein shown and described in what is conceived to be the most practical and preferred embodiments, it is recognized that departures may be made therefrom within the scope of the invention which is not to be limited to the illustrative details disclosed.

Having described our invention, what we claim as new and desire to secure by Letters Patent is:

1. A method for temporarily isolating a dental implant mounted in a jawbone and gum tissue of a patient after using an impression material to obtain an impression of an abutment portion of the dental implant and adjacent teeth and gum tissue, the implant comprising an outwardly extending annulus substantially thereabout, and the abutment portion having a proximal end and a distal end, the proximal end being proximate the annulus, the method comprising:
   removing the impression material from the dental implant, leaving the abutment portion of the dental implant substantially exposed;
   after removing the impression material and before mounting a permanent prosthesis to the abutment portion, encapsulating at least the substantially exposed abutment portion of the dental implant and the outwardly extending annulus with a housing different from the permanent prosthesis to be supported by the implant, by fixedly attaching the housing to the dental implant utilizing a recess engaged by a projection, the recess and projection being below the gum line, wherein the housing comprises an outwardly tapered portion extending from an origin proximate the annulus to a terminus and having a height from the origin to the terminus sufficient to extend above the gum line;
   wherein the encapsulating comprises establishing an outwardly tapered zone of isolation around the abutment portion and said annulus by the outwardly tapered portion of the housing, the zone of isolation extending above said annulus, through the gum line, to resist incursion of the gum tissue into said area and onto said annulus; and then
   removing the housing after a permanent prosthesis is formed based, at least in part, on the removed impression material, to again substantially expose the abutment portion; and
   mounting the permanent prosthesis to the again substantially exposed abutment portion.

2. The method of claim 1, wherein the fixedly attaching step is obtained by pressing the housing onto the implant until the recess and projection come into registry and the projection and recess snap together.

3. The method of claim 2, wherein the projection is defined, at least in part, by the annulus and the recess is defined by an inner surface of the housing, the method further comprising:
   flexing the recess over the projection to fixedly attach the housing to the implant.

4. The method of claim 3, comprising:
   flexibly snapping the recess over the projection to fixedly attach the housing to the implant.

5. The method of claim 1, further comprising:
   mounting a temporary dental appliance on the housing.

6. The method of claim 1, further comprising:
   attaching the permanent dental appliance directly to the again substantially exposed abutment portion, after removing the housing.

7. The method of claim 1, wherein the housing comprises plastic.

8. The method of claim 1, wherein the housing further comprises a second, inwardly tapered portion originating proximate the terminus of the first portion and terminating proximate the distal end of the abutment portion.

9. The method of claim 8, comprising:
   supporting the permanent prosthesis, at least in part, by a beveled surface between the first outwardly tapered portion and the second, inwardly tapered portion.

10. A method for temporarily isolating a dental implant mounted in a jawbone and gum tissue of a patient after using an impression material to obtain an impression of an abutment portion of the dental implant and adjacent gum tissue, the dental implant comprising an outwardly extending annulus substantially thereabout, the method comprising:
    removing the impression material from the dental implant, leaving the abutment portion of the dental implant substantially exposed; and then
    after removing the impression material, encapsulating at least a portion of the abutment portion of the dental implant with a first portion of a plastic housing and encapsulating at least the outwardly extending annulus with a second portion of the housing by pressing the housing onto the implant until a recess and a projection come into registry and the projection and recess snap together, below the gum line, the second portion of the housing being thicker than the first portion of the housing and having a height extending between a first end of the second portion of the housing, proximate the annulus, and a second end of the second portion of the housing; and
    occluding an area by the second portion of the housing defined by at least a portion of the height of the second portion and the thickness of the second portion to resist incursion of the gum tissue into the area and onto said annulus, the second portion having a sufficient height to extend above an upper surface of the gum tissue.

11. The method of claim 10, further comprising: mounting a temporary dental appliance on the housing.

12. The method of claim 10, wherein the implant member comprises an outwardly tapered surface terminating at the annulus and an inwardly tapered surface originating at the annulus, the method further comprising:
    occluding the area by a second portion of the housing originating at the annulus and being outwardly tapered in a direction toward the second end of the second portion, continuing the outward taper of the outwardly tapered surface of the implant member, wherein the annulus defines the widest circumference of the implant member.

13. The method of claim 12, comprising:
    encapsulating at least the abutment portion of the dental implant and the annulus during a period of time at least sufficient to fabricate a permanent dental appliance to be mounted on the dental implant or for osseointegration of the dental implant of the jawbone.

14. The method of claim 10, further comprising:
    creating a permanent dental appliance based, at least in part, on the removed impression;
    removing the housing to again substantially expose the abutment portion; and
    attaching the permanent dental appliance to the again substantially exposed abutment portion of the dental implant.

15. A method for isolating a dental implant mounted in a jawbone of a patient:
    applying impression material to an abutment portion of a dental implant mounted in the jawbone of a patient to obtain an impression of an abutment portion of the dental implant and adjacent gum tissue, the dental implant having an outwardly extending annulus substantially thereabout;

removing the impression material, leaving the abutment portion substantially exposed;

after removing the impression material and before mounting a permanent prosthesis to the abutment portion, encapsulating at least the substantially exposed abutment portion of the dental implant and the outwardly extending annulus with a housing via a snap fit between the housing and the annulus after removing the impression material and before mounting a permanent prosthetic; and establishing a zone of isolation with respect to the abutment portion and the annulus by the housing, the zone of isolation starting proximate the annulus and extending a sufficient distance from the annulus to protrude from the gum line, preventing intrusion of gum tissue into the zone of isolation; and then:

removing the housing from the abutment after a permanent prosthesis is formed based, at least in part on the removed impression material, again substantially exposing the abutment portion; and attaching the permanent prosthesis to the again substantially exposed abutment portion.

16. The method of claim 15, comprising establishing a conical shaped zone of isolation by an outwardly tapered surface of the housing, the outwardly tapered surface extending the sufficient distance to protrude from the gum line.

* * * * *